(12) United States Patent
Misra et al.

(10) Patent No.: US 8,264,681 B2
(45) Date of Patent: Sep. 11, 2012

(54) METHODS AND APPARATUS FOR REMOTE RAMAN AND LASER-INDUCED BREAKDOWN SPECTROMETRY

(75) Inventors: Anupam Kumar Misra, Honolulu, HI (US); Shiv Kumar Sharma, Honolulu, HI (US); Paul Grandmont Lucey, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 237 days.

(21) Appl. No.: 12/639,393

(22) Filed: Dec. 16, 2009

(65) Prior Publication Data

US 2010/0171951 A1    Jul. 8, 2010

Related U.S. Application Data

(60) Provisional application No. 61/204,373, filed on Jan. 5, 2009.

(51) Int. Cl.
*G01J 3/44* (2006.01)
(52) U.S. Cl. ........................................ 356/300; 356/301
(58) Field of Classification Search .................. 356/300, 356/301, 311, 326
See application file for complete search history.

(56) References Cited

U.S. PATENT DOCUMENTS

2008/0198365 A1*   8/2008   Treado et al. .................. 356/73

* cited by examiner

*Primary Examiner* — Tara S Pajoohi Gomez
(74) *Attorney, Agent, or Firm* — Foley & Lardner LLP; Stephen E. Reiter

(57) ABSTRACT

An spectrometer including Raman and LIBS spectroscopy capabilities is disclosed. The spectrometer includes a laser source configurable to produce a lased light directable towards a target substance, the laser source having a single wavelength and having sufficient power to cause a portion of the target to emit Raman scattering and sufficient to ablate a portion of the target substance to produce a plasma plume. A separate remote light collector is optically configurable to collect light emitted from the portion of the target emitting Raman scattering and from the portion of the target producing the plasma plume. A filter is optically coupled to the remote light collector to remove reflected light and Rayleigh-scattered light, and a spectroscope is optically coupled to the filter and configured to separate the collected and filtered light into a frequency spectrum comprising a Raman spectrum and a laser-induced breakdown spectrum. Finally, an electronic light sensor is used to record the frequency spectrum.

12 Claims, 13 Drawing Sheets

METHODS AND APPARATUS FOR REMOTE RAMAN AND LASER-INDUCED BREAKDOWN SPECTROMETRY

CROSS REFERENCE TO RELATED APPLICATION

This application is a non-provisional application claiming priority from U.S. Provisional Application Ser. No. 61/204,373, filed Jan. 5, 2009, and incorporated herein by reference in its entirety.

STATEMENT OF GOVERNMENTAL SUPPORT

At least a portion of the invention disclosed and claimed herein was made in part utilizing funds supplied by Office of Naval Research under Grant No. N00014-08-1-0351. The United States Government has certain rights in this invention.

FIELD OF THE DISCLOSURE

The present disclosure relates generally to spectrometry and more particularly to methods and apparatus for remote Raman and Laser-Induced Breakdown Spectrometry.

BACKGROUND OF RELATED ART

Spectrometry is a technique used to assess the concentration or amount of a given material. The apparatus that performs such measurements is a spectrometer or spectrograph. Spectrometry is often used in physical and analytical chemistry for the identification of substances through the spectrum emitted from or absorbed by them. Spectrometry is also often used in remote sensing applications, such as explosive detection.

One example method of spectrometry is Raman spectroscopy. Raman spectroscopy uses the inelastic scattering of light to analyze vibrational and rotational modes of molecules. Because vibrational information is specific to the chemical bonds, atomic mass of the atoms in the bond and symmetry of molecules, Raman spectroscopy provides a "fingerprint" by which the molecule can be identified.

Another example method of spectrometry is Laser-induced breakdown spectrometry (LIBS). LIBS uses a high-power laser focused onto the surface of a sample to produce plasma. Light from the plasma is captured by spectrometers and the characteristic spectra of each element can be identified, allowing concentrations of elements in the sample to be measured.

DETAILED DESCRIPTION

Figure 1:
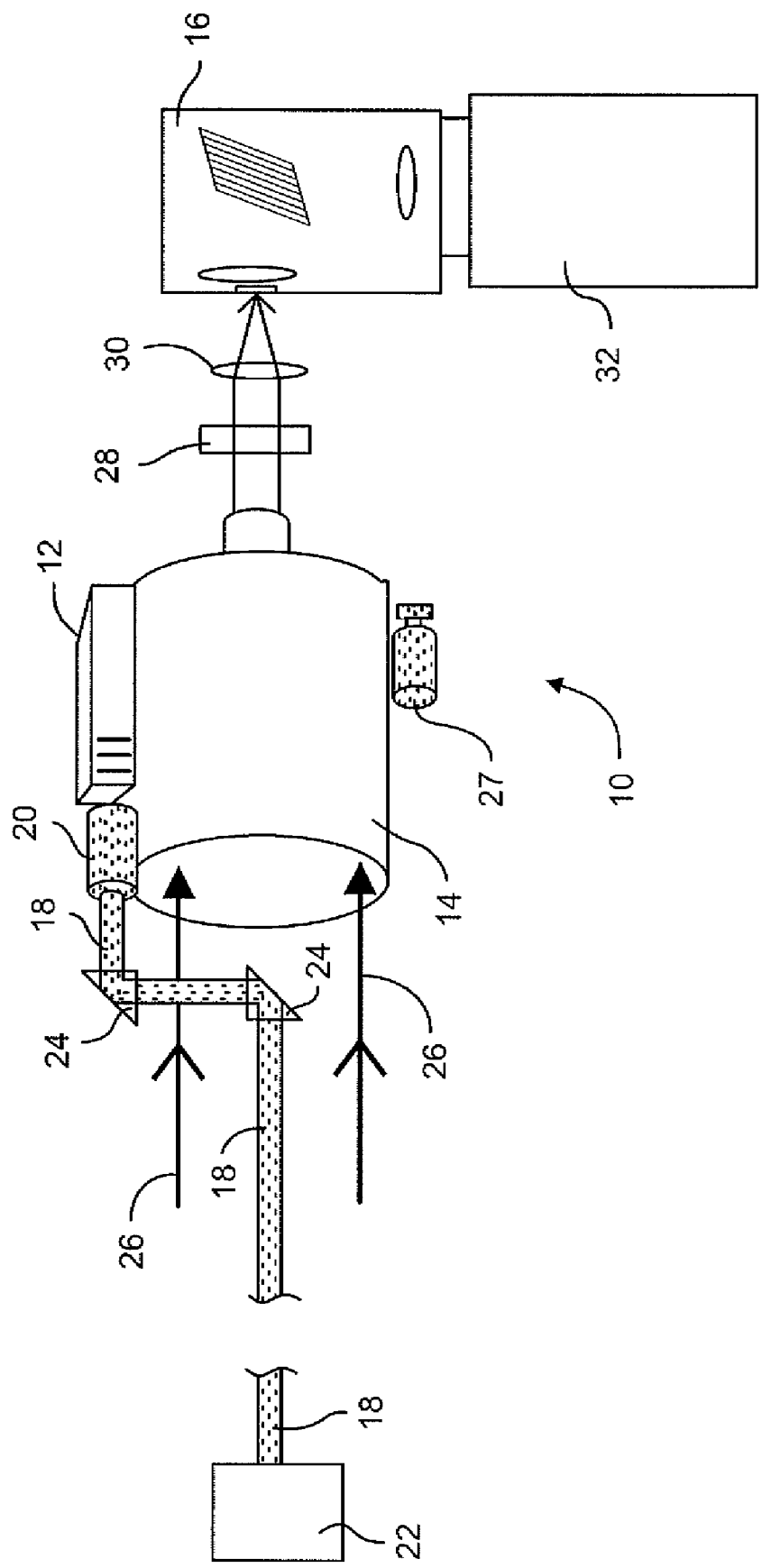
FIG. 1 is an illustration of an example apparatus suitable for measuring remote LIBS and Raman spectra.

The following description of the disclosed examples is not intended to limit the scope of the invention to the precise form or forms detailed herein. Instead the following description is intended to be illustrative of the principles of the invention so that others may follow its teachings.

Raman spectroscopy typically uses either a continuous wave (CW) or a pulse visible laser of modest average power (e.g., approximately 100-700 $mW/cm^2$) to identify the molecular fingerprint of the sample from its Raman spectrum. For a continuous wave laser based remote Raman system, there are generally two significant issues: interference of the high-ambient light background during the day; and long-lived fluorescence with the Raman spectra of the sample. However, as described herein, by utilizing a pulsed laser system and gated receiver, these limitations may be overcome. Pulsed Raman spectroscopy offers two important benefits: the ability to discriminate against unwanted light; and the ability to discriminate against long-lived fluorescence emissions from the sample.

In general, LIBS uses a pulsed laser having a typical wavelength of 1064 nm, and a high peak power (e.g., >1 GW/cm.sup.2) for ablating material from the surface of a sample and to probe elemental composition. During LIBS, a small amount of the target is ablated and atomized, and the resulting atoms are excited to emit light. The emitting elements are identified by their unique spectral peaks, and the process yields semi-quantitative abundances of major, minor, and trace elements simultaneously. Advantageously, laser ablation profiles through dust and weathering layers, meaning that the LIBS technique is effective in cleaning sample surfaces. By repetitive sampling with a high intensity laser at the same spot, the LIBS technique permits ablation through weathered surfaces to reach the underlying bulk rock.

Both remote Raman and remote LIBS spectroscopic techniques interrogate samples using pulsed laser beams and both employ dispersive spectrographs over over-lapping spectral ranges with approximately the same spectral resolution. Therefore, as described herein, it is possible to combine the two techniques into one system. In particular, at low laser power density at the sample, one obtains the Raman spectra and at high laser power, with high optical power density, one can also generate the LIBS plasma spectra and record the LIBS spectra from the same material. Both the Raman and LIBS spectra can be recorded simultaneously with a focused laser where the area falling in the high energy density region produces the LIBS spectra and molecules exited by the edges of the focused beam corresponding to a low energy density region generates the Raman spectra.

By combining remote Raman spectroscopy and remote LIBS in a single apparatus a more complete analysis of a sample in terms of mineralogy and elemental composition is possible. For example, Raman spectroscopy can determine whether the sample is calcite or aragonite, both of which have the same chemical composition but different mineral structures that often indicate different geological formation processes. LIBS analysis is sensitive to typical cationic elements and is also capable of remotely detecting hydrogen, carbon, oxygen, and sulfur. Raman spectroscopy mostly distinguishes mineral structure and anionic species from Raman active lattice modes of the mineral, and can provide only indirect information about cations from internal vibrational mode of polyatomic cations that are sensitive to cationic composition. Usually Raman active lattice modes are much more sensitive to composition and polymorphism than the internal modes of vibrations.

Additionally, for the detection of organic compounds, Raman spectroscopy is a more desirable technique than LIBS as it can distinguish between various hydrocarbons such as benzene, naphthalene, methane, and their various chemical isomers (e.g., o-, m-, p-xylene, etc.); and different kind of organic molecules, such as protein, lipids, amino acids, complex molecules such as pigments, mycosporines, etc.

Moreover, LIBS can detect small amounts of impurities in a bulk sample, but the trace analysis is difficult with Raman spectroscopy because the Raman signal is proportional to the number of molecules excited by the laser in the sample. A few molecules of impurity produce a very small Raman signal compared to the signal produced by the host bulk sample.

Accordingly, there is a desire to combine the two techniques and to develop various methods and apparatus that include a single instrument capable of analyzing a sample from a remote distance and capable of obtaining both Raman and LIBS spectra. The combined Raman and LIBS methods and apparatus described herein may be used for a variety of applications, including, for example, in the remote identification of explosives, explosive residue, chemical, minerals, gases, fume clouds, and/or other chemicals of interest. Additionally, by providing for a remote sensing capability, the described apparatus and/or operator may be located a distance away from the sample, providing for a greater range of detection and/or safety.

Referring now to FIG. 1, a diagram illustrating an example combined Raman spectroscopy and LIBS apparatus 10 is shown. The example apparatus 10 generally includes a laser source 12, an emitted light collector 14, and a spectrograph 16. Specifically, in this example, the laser source 12 emits a lased light such as, for example, a laser beam 18. The example laser beams 18 may travel through a beam expander 20 to focus and shape the laser beam as desired. The resultant laser beam 18 is then directed toward the intended remote target 22. In this example, a plurality of prisms 24 are used to direct the laser beam 18, however, any suitable object, device, and/or means of directing the beam 18 may be utilized including, for example, a splitter, mirror(s), etc. In each example, the laser beam 18 is of sufficient power to cause the generation of an emission signal 26 at the target 22 having at least one of Raman excitation and LIBS plasma formation as described herein.

As noted, Raman excitation generally relies upon inelastic scattering, or Raman scattering, of the laser beam 18, such as, for instance, the vibrational, rotational, and/or other low-frequency excitation modes in the target 22. In particular, the laser light 18 interacts with molecular vibrations or other excitations in the target 22, resulting in the energy of the laser photons being shifted up or down. The shift in energy gives detectable information (e.g., the signal 26) about the Raman active vibrational and rotational modes in the target 22.

Similarly, as described, LIBS operates by focusing the laser beam 18 onto a small area at the surface of the target 22. During LIBS, the laser beam 18 is of sufficient power to ablate at least a portion of the target 22 to generate a detectable plasma plume. In particular, as the plasma plume expands and cools, the plume emits atomic emission lines (e.g., the signals 26) characteristic of the elements comprising the target 22.

After the laser beam 18 strikes the target 22, the emitted signals 26 (e.g., at least one of Raman and/or LIBS) excited by the laser beam 18 are collected by the collector 14. The example collector 14 may be any suitable collector, including, for instance, a telescope. In this example, the telescope includes a beam finder 27 which may be used to align the telescope with the beam 18. The collected signals 26 are then optically directed into the spectrograph 16 for processing. In at least one example, however, the collected signals 26 are first passed through a filter 28, such as, for example, a notch filter to remove the reflected and Rayleigh-scattered light from the signal 26. Additionally, in this example, the signal 26 is focused into the spectrograph 16 by passing through at least one lens 30. The example signal 26 may then be processed by the spectrograph 16. In particular, the spectrograph 16 is configured to separate the signal 26 into a detectable frequency spectrum. For example, to detect the generated frequency spectrum, the example apparatus 10 includes an intensified charge-coupled device (ICCD) 32 optically coupled to the spectrograph 16. Once detected by the ICCD 32, the frequency spectrum may be processed by any suitable process, including, for example, by spectrum analysis software.

In one example of the integrated remote Raman and LIBS apparatus 10, the laser source 12 is a frequency doubled mini Nd:YAG laser source, such as a Model ULTRA CFR, Big Sky Laser, 532 nm, 20 Hz. The use of a double pulse separated, by, for example approximately 0.15.mu.s to approximately 1.0.mu.s may enhance the LIBS signal by at least a factor of 10. The example 532 nm pulsed laser beam is focused to a spot (e.g., 300.mu.m diameter) on the target 22 placed a distance (e.g., nine meters) away with a 10.times. beam expander 20. For simple Raman measurements the laser power at 532 nm may be electronically adjusted to approximately 25 mJ/pulse, and for combined LIBS and Raman measurements the laser power may be increased to approximately 35 mJ/pulse.

In still other examples, the laser source 12 may produce a lased light with any suitable wavelength, such as, for example, 248 nm, 266 nm, 532 nm, 785 nm, and 830 nm for Raman spectra, and 532 nm and 1064 nm for LIBS spectra. Still further, it will be appreciated that a Raman spectra may first be produced at a lower laser power and/or by defocusing the laser beam, thereby giving a lower optical power density which is not enough to decompose the sample. The LIBS spectra may then be obtained after the Raman measurement on the same target with a higher laser power and/or a focused laser beam, thereby giving a high enough optical power density to ablate the sample.

In one example for the combined Raman and LIBS measurements, the signals 26 excited by the laser source 12 are collected with a 203-mm diameter reflecting telescope in 180-degree geometry, such as, for example, a Meade LX200R Advanced Ritchey-Chrétien, 203 mm clear aperture, f/10. In other example, the laser source 12 may be collected with any suitable light collector, including, for example, a suitable camera lens. Additionally, in one example, the collected signal 26 passes through a 532-nm holographic super-notch filter (NF) to remove the reflected and Rayleigh-scattered laser light, and enters the spectrograph 16, which in this example is a Kaiser F/1.8 HoloSpec transmission-grating spectroscope with a 100-μm slit coupled to an intensified CCD detector, such as a Princeton Instruments, PI-MAX. The HoloSpec spectrometer measures the Raman spectra from 70 $cm^{-1}$ to 4500 $cm^{-1}$ when excited with a 532 nm laser. The grating covers the spectral region between 534 nm to 699 nm, which is sufficient for identifying some of the major atomic emission lines of measured targets 22 from their LIBS spectra. It will be understood, however, that the components and/or operating parameters of the example apparatus 10 may be suitably changed, combined, and/or configured as desired.

Figures 2, 3:
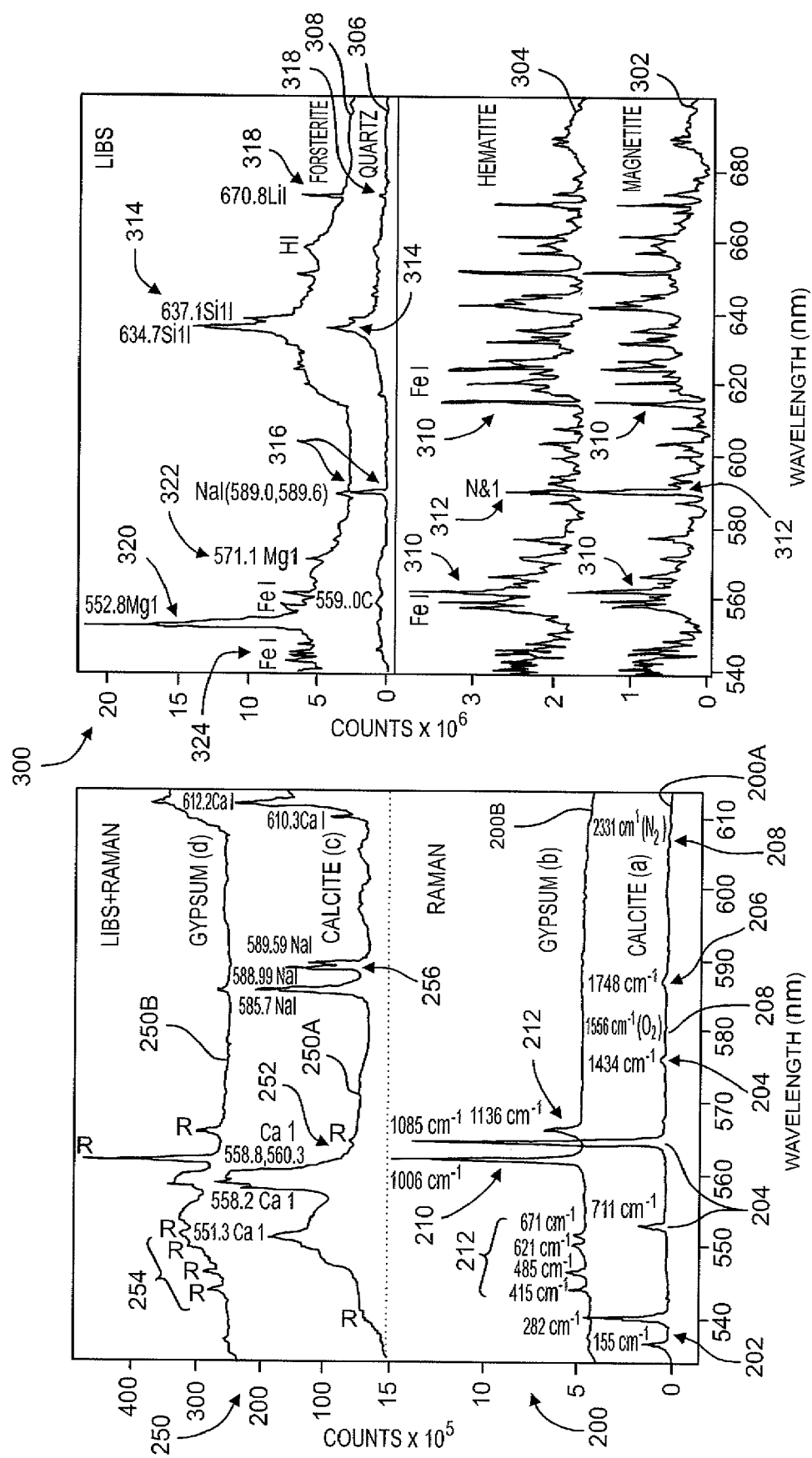
FIG. 2 is a graph illustrating one example of both Raman, and Raman/LIBS spectra as measured by the example apparatus of FIG. 1.
FIG. 3 is a graph illustrating one example of LIBS spectra as measured by the example apparatus of FIG. 1.

FIG. 2 is a graph illustrating one example of both Raman, and Raman/LIBS spectra as measured by the example apparatus 10. In particular, FIG. 2 shows a Raman spectra 200 and a combined Raman and LIBS spectra 250 of calcite ($CaCO_3$) 200A, 250A and of Gypsum ($CaSO_4.2H_2O$) 200B, 250B located at approximately nine meters in air and in the 534-615 nm wavelength range. In this example, the Raman spectra 200 of these samples were excited with 25 mJ/pulse of the 532 nm laser and accumulated for one second in the gated mode with a 2 μs gate. As illustrated, the lattice modes 202 of calcite at 155 $cm^{-1}$ and 282 $cm^{-1}$ are clearly visible, along with internal modes 204 of carbonate ions at 711 ($v_4$) $cm^{-1}$, 1085 ($v_1$) $cm^{-1}$, and 1434 ($v_3$) $cm^{-1}$. In addition, a combination mode 206 of carbonate ions at 1748 $cm^{-1}$ and the symmetric stretching modes 208 of atmospheric $O_2$ and $N_2$, respectively at 1556 $cm^{-1}$ and 2331 $cm^{-1}$ are also detected.

In the illustrated Raman spectrum of gypsum 200B, the strongest Raman peaks 210 observed at 1006 $cm^{-1}$ originate from the symmetric stretching vibrations of the $SO_4^{2-}$ ion, $v_1$ ($SO_4$), and its position depends on degree of hydration. The other internal mode of vibration of sulfate ions 212 appear at 1136 (v3) $cm^{-1}$, 415 $cm^{-1}$ and 495 (v2) $cm^{-1}$, and 621 $cm^{-1}$ and 671 (v4) $cm^{-1}$ are clearly visible.

In the combined LIBS and Raman spectra 250 of calcite 250A and of gypsum 250B the Raman lines are marked with the letter "R". In the example spectrum of calcite 250A, the 1085 $cm^{-1}$ Raman line of carbonate 252 appears only as a weak line. In the example combined LIBS and Raman spectra of gypsum 250B, most of the prominent Raman lines of sulfate 254 are clearly visible indicating that the LIBS spectrum is produced only by a few hot spots in the focused laser beam. As both calcite and gypsum contain Ca cations, the LIBS lines 250 in FIG. 2 originate from Ca I excited states. In the combined LIBS Raman spectrum of calcite 250A the LIBS lines 256 at 588.99 and 589.59 nm indicate presence of trace amount of Na ion in the calcite sample.

Similarly, FIG. 3 is a graph illustrating one example of LIBS spectra as measured by the example apparatus 10. Specifically, FIG. 3 shows an example of a remote LIBS spectrum 300 of minerals magnetite ($Fe_3O_4$) 302, hematite ($Fe_2O_3$) 304, α-quartz (α-$SiO_2$, Qz) 306, and forsterite ($Mg_2SiO_4$, Fo) 308, respectively. The example graph is limited to the 540-690 nm spectral range, the respective target was located approximately nine meters away, and was excited with a 532 nm laser pulse of 35 mJ/pulse. The LIBS illustrated spectra 300 of magnetite 302 and hematite 304 and are dominated by the Fe I emission lines 310. Both of these iron oxides contain a few ppm of Na as indicated by the presence of Na I emission lines 312 at 589.0 and 589.6 nm.

Additionally, the remote LIBS spectra of Fo 308 and Qz 310 show strong emission lines of Si 314 at 634.7 and 637.1 nm, and weak emission lines of Na 316 and Li 318 indicate the presence of these elements in trace amounts. The Fo LIBS spectrum 308 contains strong emission lines of Mg 320 at 552.8 nm and a weak line 322 at 571.1 nm. A number of weak Fe emission lines 324 are also observed in the LIBS spectrum of Fo indicating that this sample is indeed Mg-rich olivine (Fo 92) containing about 8% of iron.

Figure 4:
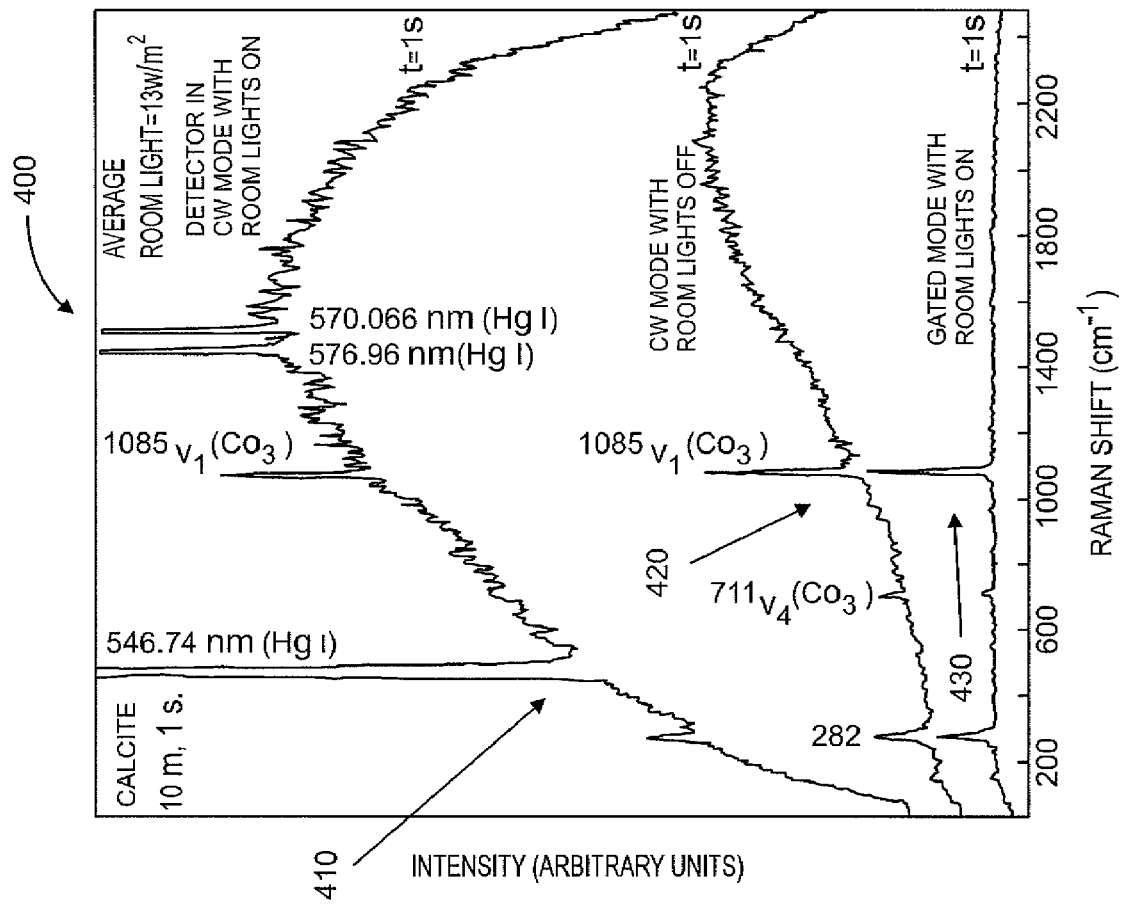
FIG. 4 is graph of another example data set measured by the example apparatus of FIG. 1.

In another example data set reproduced as a graph 400 in FIG. 4, another operation of the example apparatus 10 is illustrated. In this example, the apparatus 10 was used to detect the Raman shift of calcite at a distance of approximately ten meters, using only a Raman spectrum. In a first operating example 410, the apparatus 10 was operated in a continuous wave mode with room lights on and having an average room light of 13 $W/m^2$. In a second operating example 420, the apparatus 10 was again operated in a continuous wave mode with the room lights turned off. Finally, in a third operating example 430, the apparatus 10 was operated in a gated mode, with the room lights turned on and having an average room light of 13 $W/m^2$.

Figure 5:
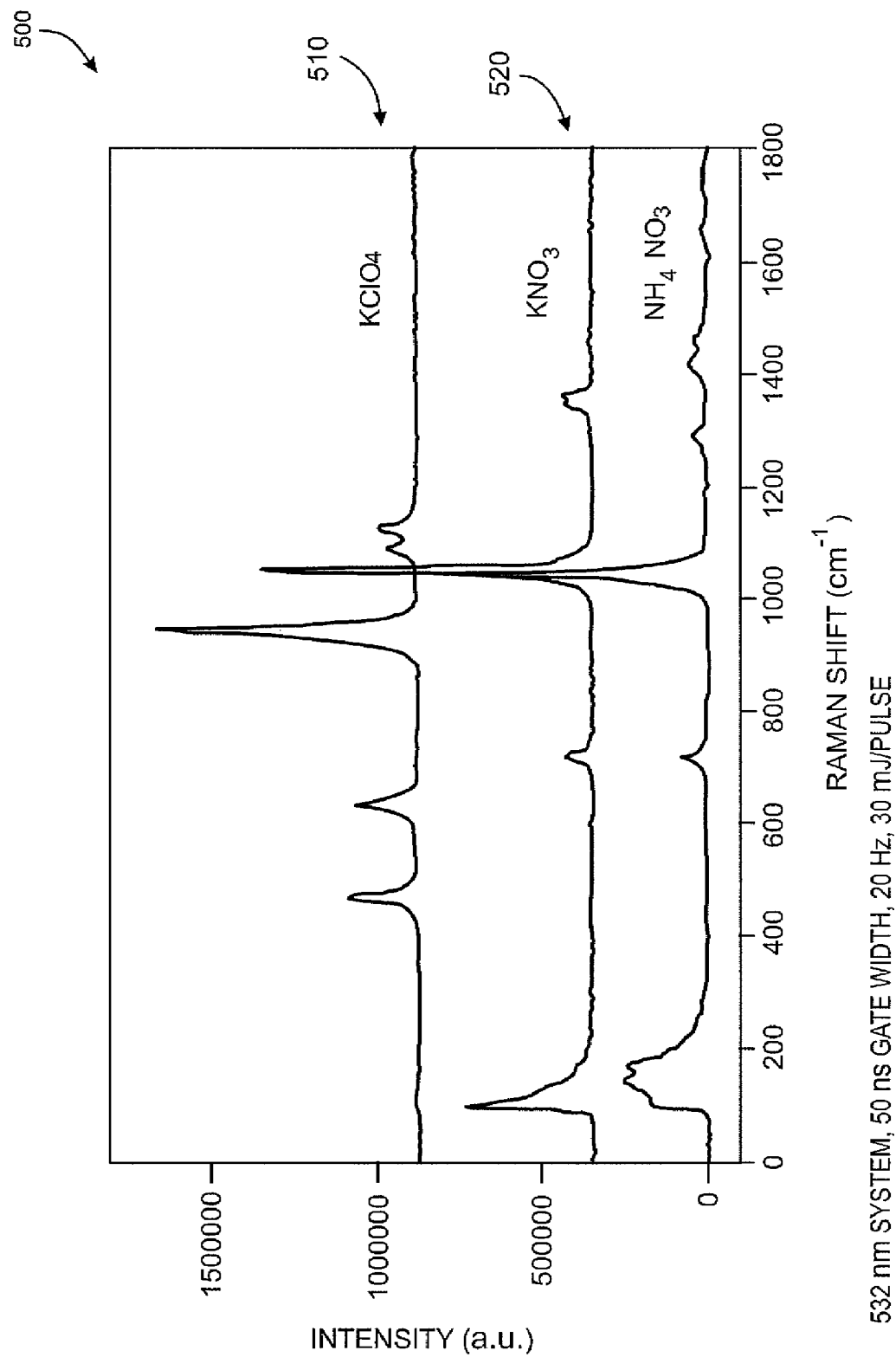
FIG. 5 is graph of another example data set measured by the example apparatus of FIG. 1.

In another example use of the apparatus 10 illustrated as a graph 500 in FIG. 5, the apparatus 10 was used to detect the Raman shift of a homemade explosive chemical at a distance of approximately fifty meters. The laser 12 of the example apparatus 10 was operated at 532 nm, 20 Hz, 30 mJ/pulse, and included a 50 ns gate width. In a first example 510, the apparatus 10 was utilized to detect potassium perchlorate ($KClO_4$). In a second example 520, the apparatus 10 was utilized to detect potassium nitrate ($KNO_3$). Finally, in a third example 530, the apparatus 10 was used to detect ammonium nitrate ($NH_4NO_3$). In each example, the apparatus 10 provided clear, sharp peaks for chemical identification, with a high signal-to-noise ratio.

Figure 6:
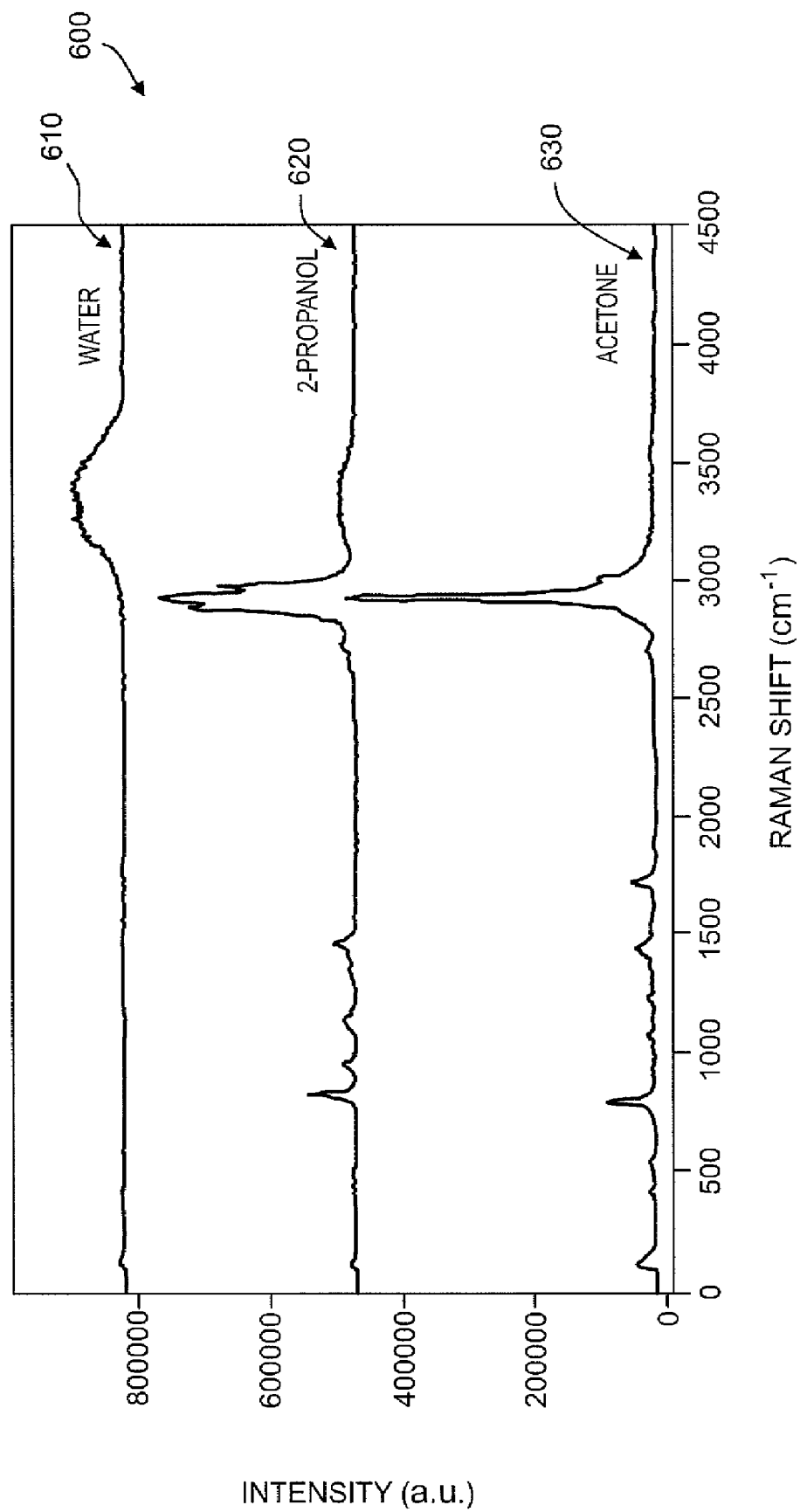
FIG. 6 is graph of another example data set measured by the example apparatus of FIG. 1.

In yet another example use of the apparatus 10 illustrated as a graph 600 in FIG. 6, the apparatus 10 was used to detect the Raman shift of various chemicals through a container at a distance of approximately fifty meters. In a first example 610, the apparatus 10 was utilized to detect water ($H_2O$). In a second example 620, the apparatus 10 was utilized to detect isopropyl alcohol (2-propanol). Finally, in a third example 630, the apparatus 10 was used to detect acetone ($OC(CH_3)_2$). In each example, the apparatus 10 was able to detect the various liquids through plastic and/or glass containers.

Figure 7:
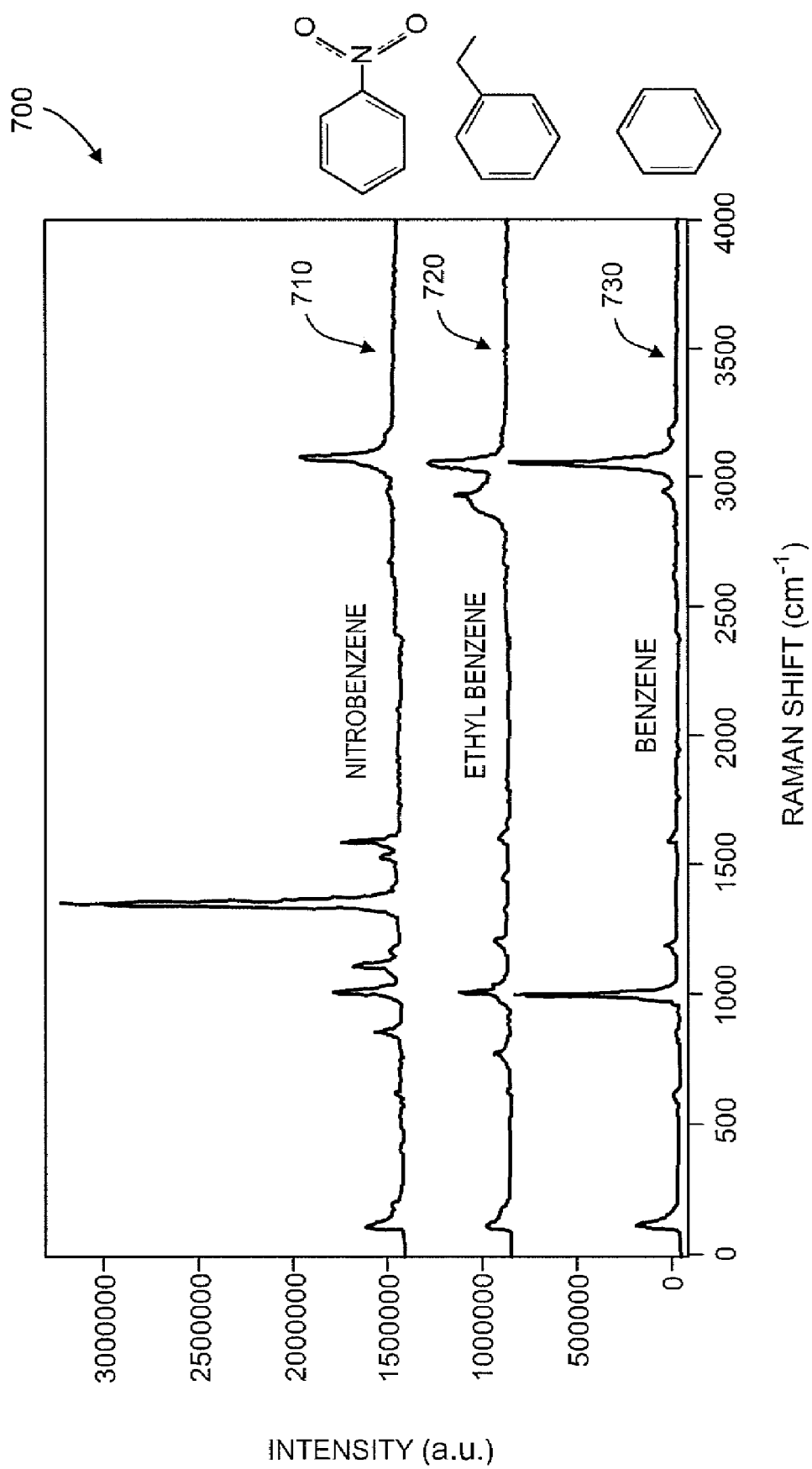
FIG. 7 is graph of another example data set measured by the example apparatus of FIG. 1.

In still another example use of the apparatus 10 illustrated as a graph 700 in FIG. 7, the apparatus 10 was used to detect and distinguish between the Raman shift associated with similar chemical, during daytime and at a distance of approximately fifty meters. In a first example 710, the apparatus 10 was used to detect nitrobenzene ($C_6H_5NO_2$). In a second example 720, the apparatus 10 was utilized to detect ethylbenzene ($C_6H_5CH_2CH_3$). Finally, in a third example 630, the apparatus 10 was used to detect benzene ($C_6H_6$).

Figure 8:
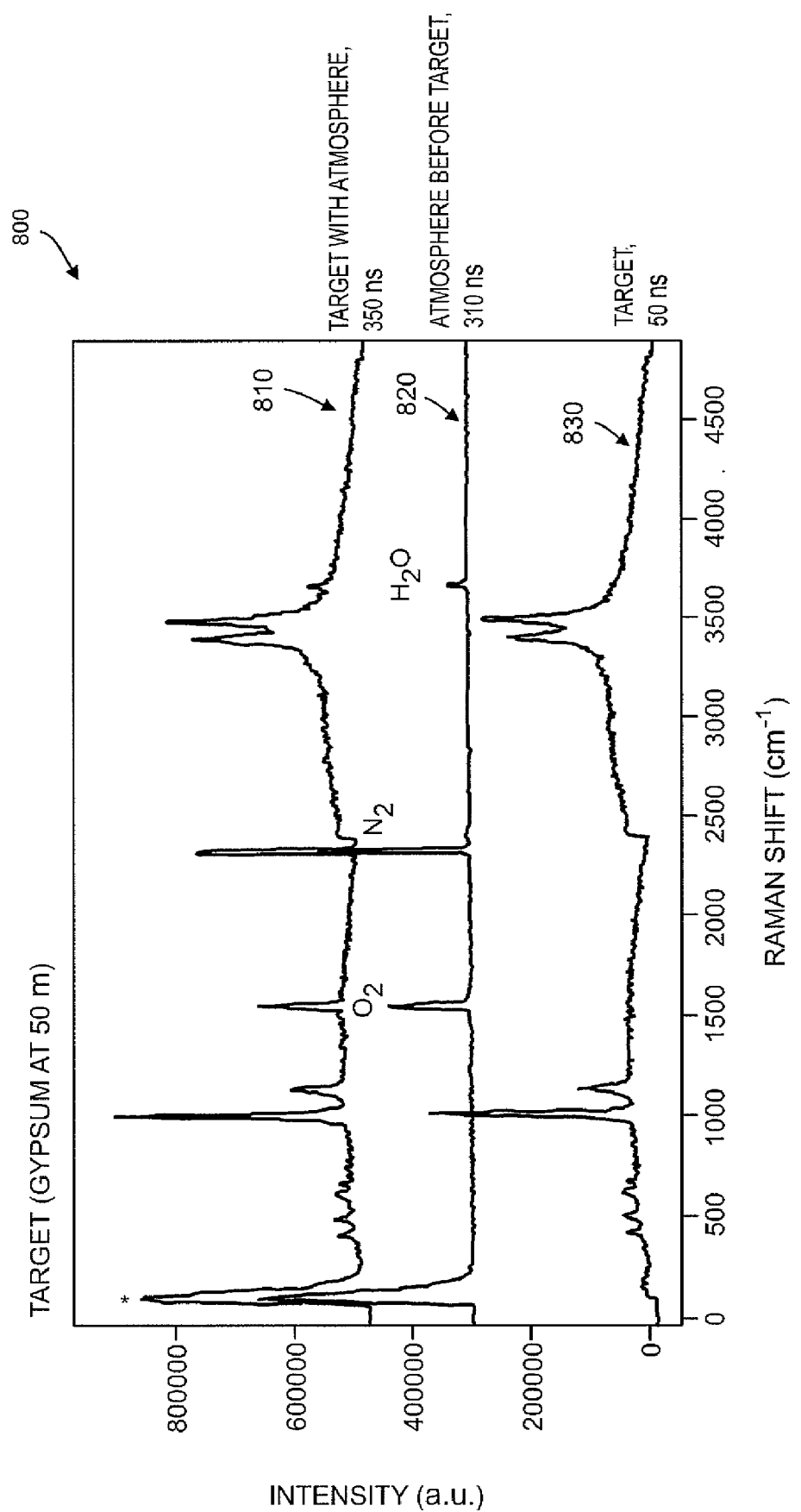
FIG. 8 is graph of another example data set measured by the example apparatus of FIG. 1.

As illustrated in a graph 800 in FIG. 8, in another example, the apparatus 10 was used to detect gypsum at approximately fifty meters. In this example, the apparatus 10 was used to detect the Raman shift of both the target gypsum and/or the ambient atmosphere. In particular, in a first example 810, the apparatus 10 was used to detect both the ambient atmosphere and the gypsum target. In a second example 820, the apparatus 10 was used to detect only the ambient atmosphere. Lastly, in a third example 830, the apparatus 10 was used to detect only the gypsum target.

Figure 9:
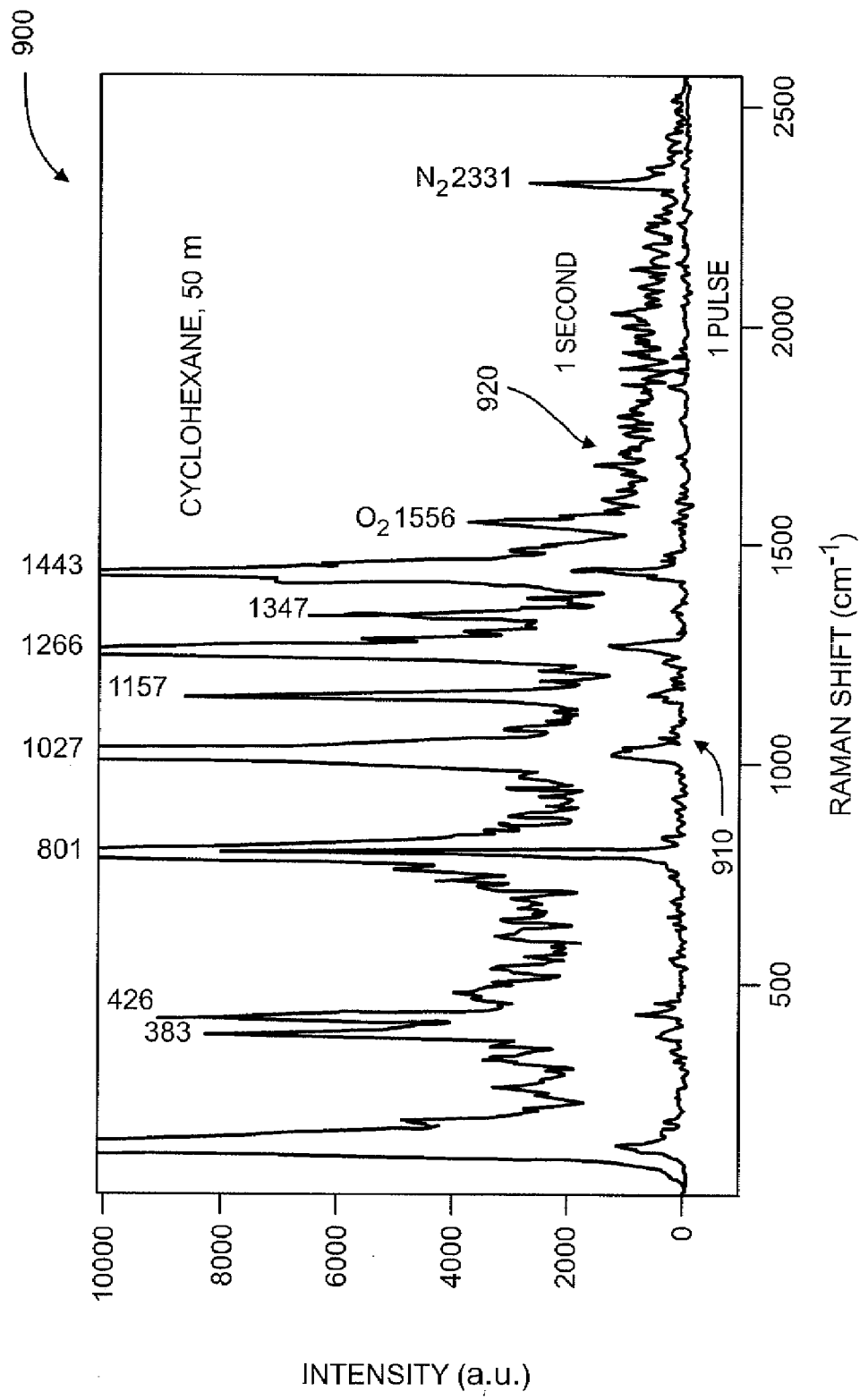
FIG. 9 is graph of another example data set measured by the example apparatus of FIG. 1.

In another example use of the apparatus 10 illustrated as a graph 900 in FIG. 9, the example apparatus 10 was used both in a single pulse mode 910, and in a one-second, twenty pulse mode 920. In this example, the apparatus was used to detect the Raman shift of cyclohexane ($C_6H_{12}$) at a distance of approximately fifty meters. As is illustrated, the detected signals 910 and 920 are proportional to the number of laser pulses.

Figure 10:
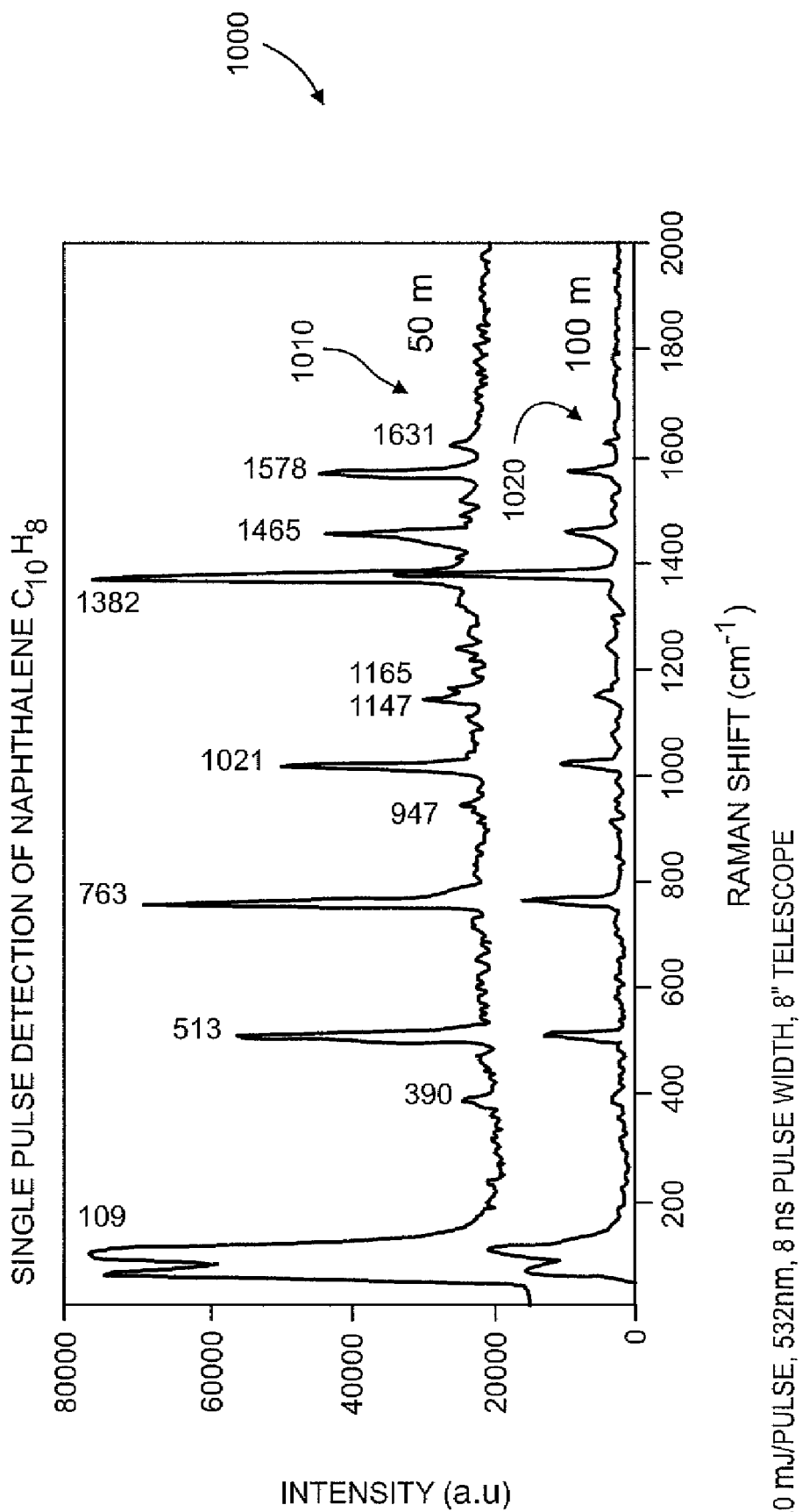
FIG. 10 is graph of another example data set measured by the example apparatus of FIG. 1.

In still another example use of the apparatus 10 illustrated as a graph 1000 in FIG. 10, the example apparatus 10 was used to detect the Raman Shift of naphthalene ($C_{10}H_8$). In a first example 1010 the apparatus 10 was placed approximately fifty meters from the target naphthalene. In a second example 1020 the apparatus 10 was placed approximately one hundred meters from the target naphthalene. As is shown, the detected signals 1010 and 1020 are substantially similar in shift detection and proportional in intensity.

Figure 11:
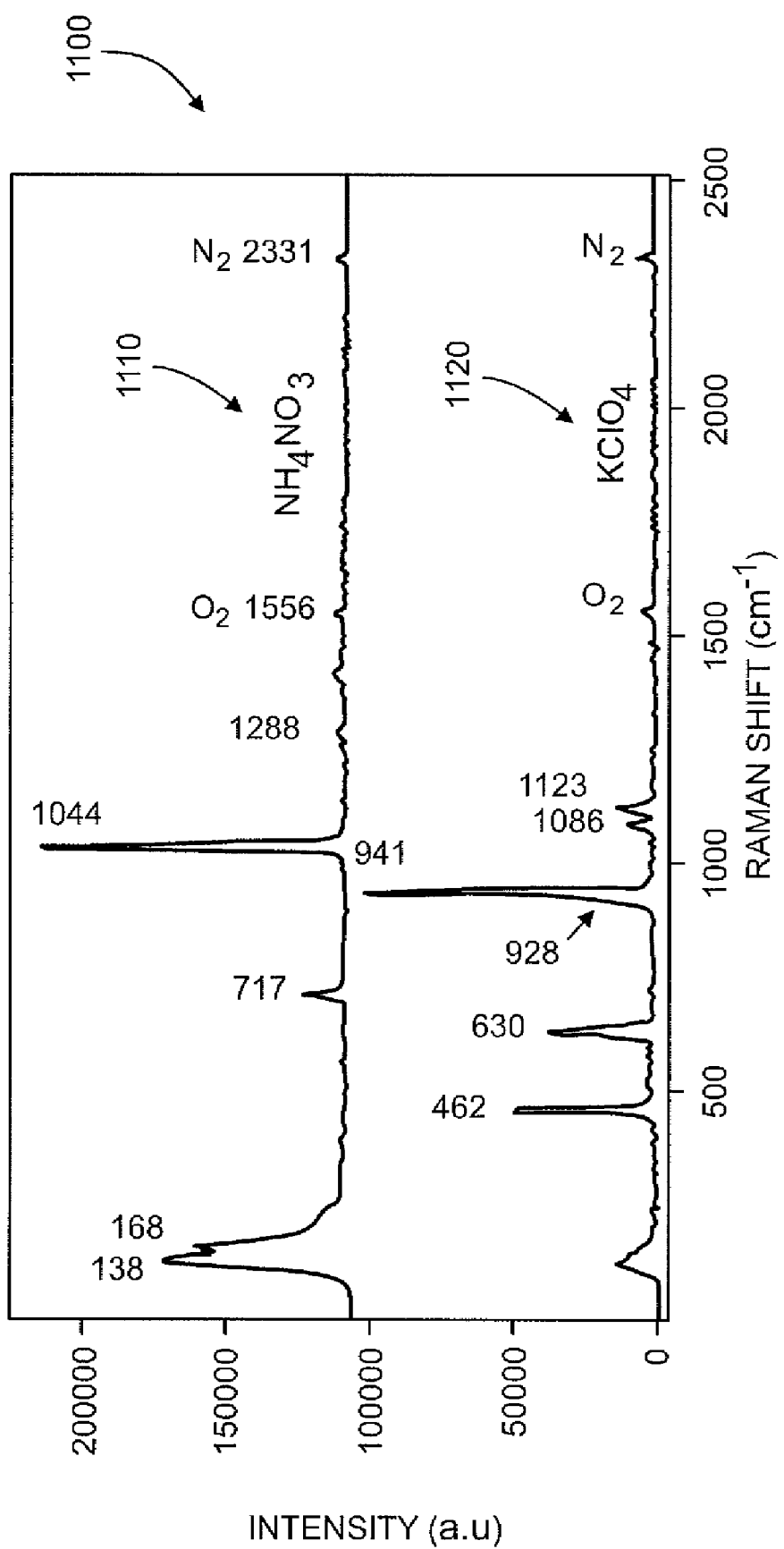
FIG. 11 is graph of another example data set measured by the example apparatus of FIG. 1.

In another example data set reproduced as a graph 1100 in FIG. 11, the example apparatus 10 was used to detect the Raman shift of a target at a distance of approximately one hundred meters. In a first operating example 1110, the apparatus 10 was used to detect ammonium nitrate ($NH_4NO_3$). In a second operating example 1120, the example apparatus 10 was used to detect Potassium perchlorate ($KClO_4$).

Figure 12:
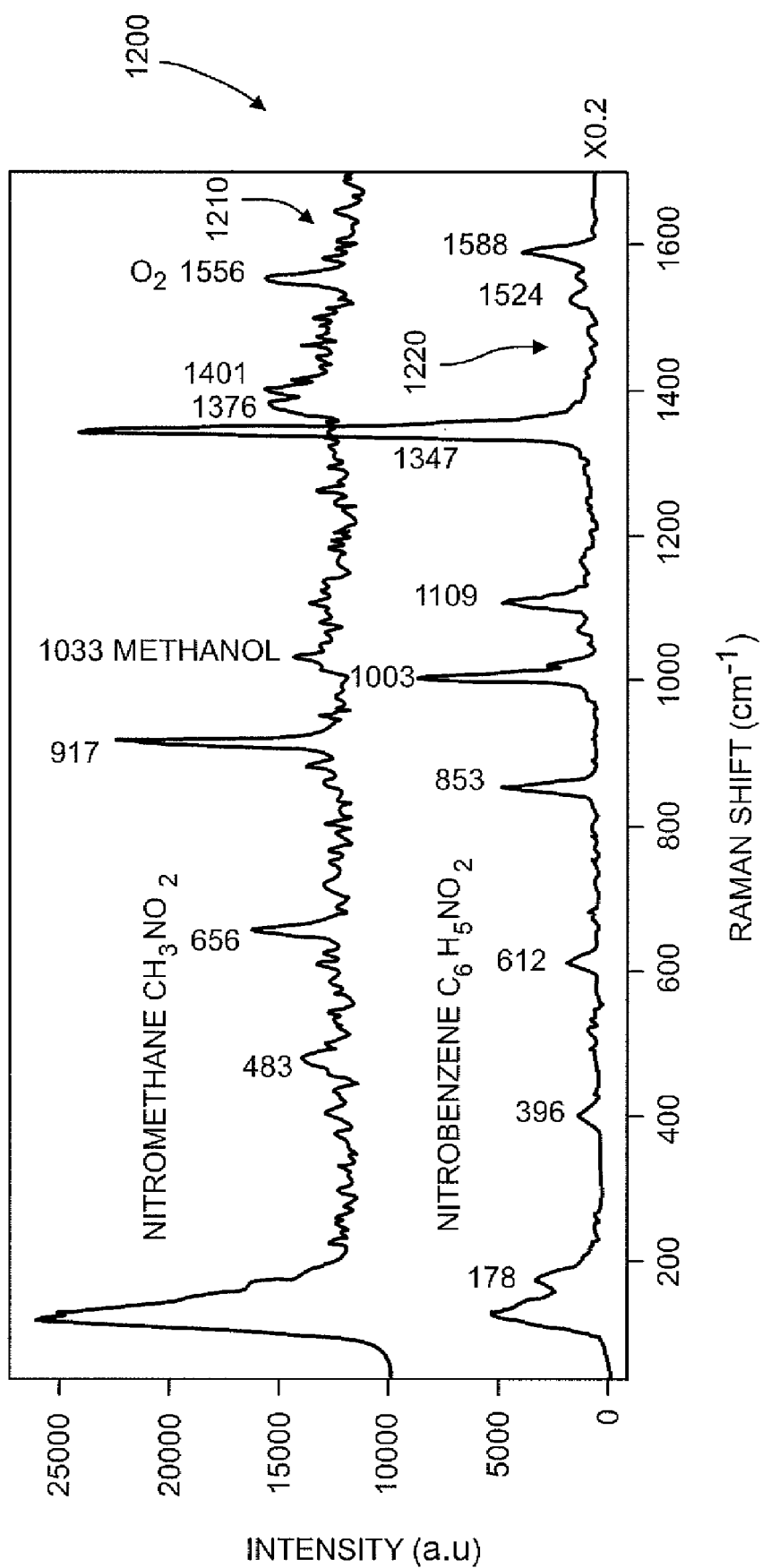
FIG. 12 is graph of another example data set measured by the example apparatus of FIG. 1.

In another example data set reproduced as a graph 1200 in FIG. 12, the example apparatus 10 was used to detect the Raman shift of an organic target at a distance of approximately one hundred meters. In a first operating example 1210, the apparatus 10 was used to detect nitromethane ($CH_3NO_2$). In a second operating example 1220, the example apparatus 10 was used to detect Nitrobenzene ($C_6H_5NO_2$) and is graphed at ×0.2.

Figure 13:
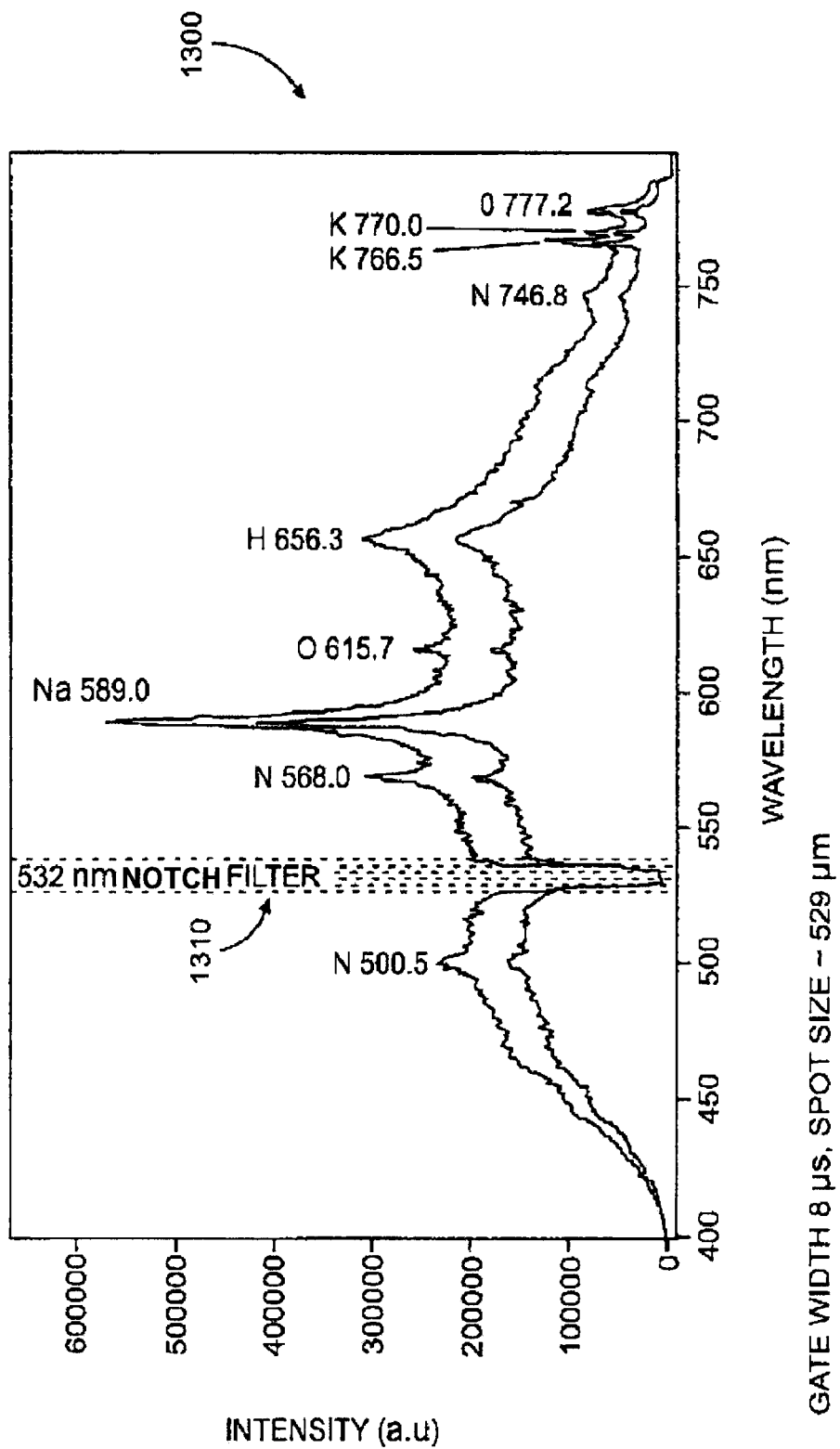
FIG. 13 is graph of another example data set measured by the example apparatus of FIG. 1.

In an example data set reproduced as a graph 1300 in FIG. 13, the results of the operation of the example apparatus 10 is illustrated. In this example, the apparatus 10 was used to detect the LIBS spectrum of Trinitrotoluene (TNT) ($C_6H_2(NO_2)_3CH_3$). In this example, the LIBS spectrum was produced with a single pulse excitation of a 532 nm laser powered to 35 mJ. The target was placed at approximately nine meters from the apparatus 10. Additionally, in this example, the gate size of the detector 32 was 8.mu.s, and the produced laser spot on the target TNT was approximately 629.mu.m. As can be seen from the graph 1300, the notch filter 28 creates an area 1310 of filter (e.g., zero) data.

Figure 14:
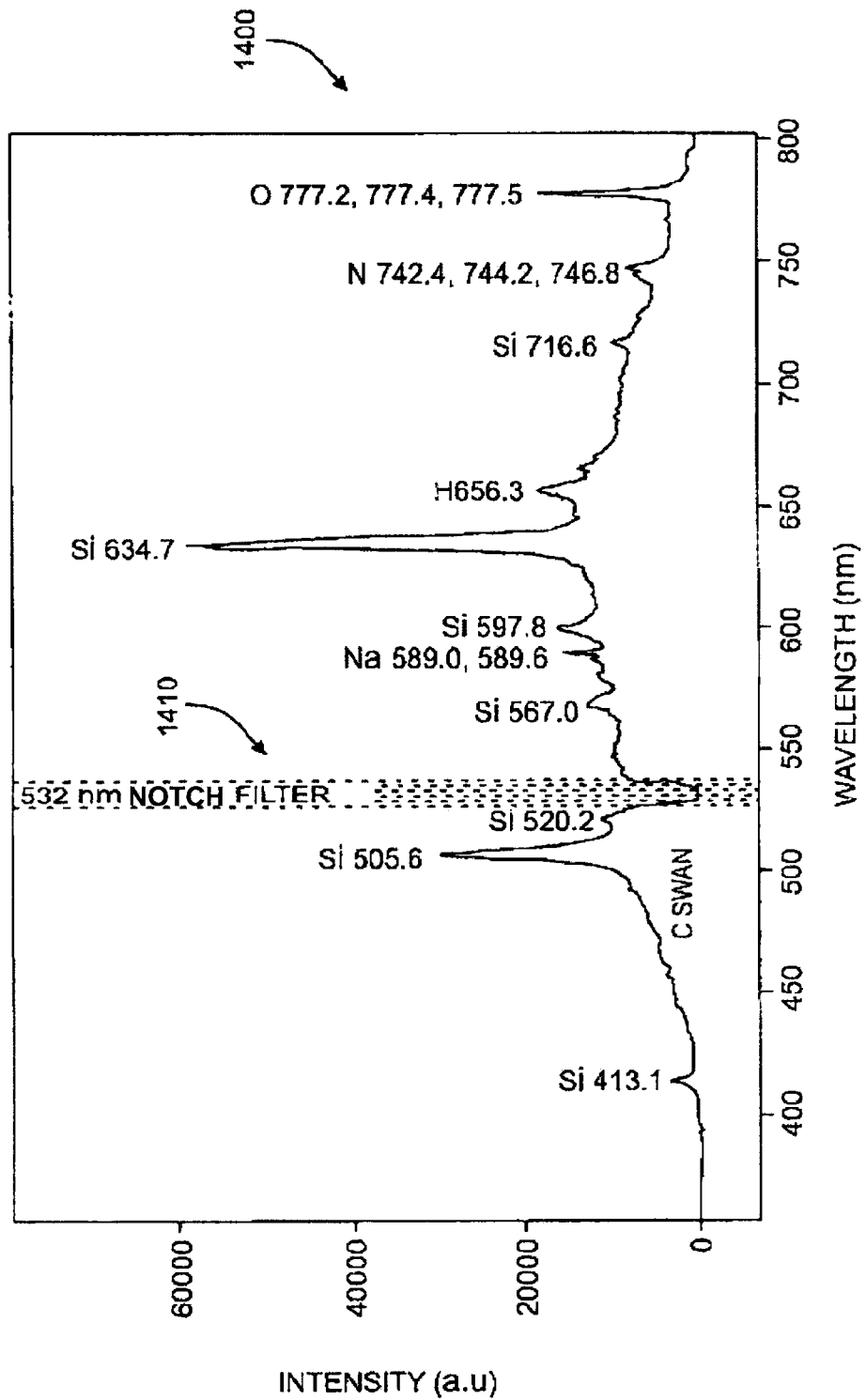
FIG. 14 is graph of another example data set measured by the example apparatus of FIG. 1.

In an example data set reproduced as a graph 1400 in FIG. 14, the result of the operation of the example apparatus 10 is illustrated. In this example, the apparatus 10 was used to detect the LIBS spectrum of eight percent Cyclotrimethylenetrinitramine (8% RDX) on silica. In this example, the LIBS spectrum was produced with a single pulse excitation of a 532 nm laser powered to 35 mJ. The target was placed at approximately nine meters from the apparatus 10. As can be seen from the graph 1400, the notch filter 28 creates an area 1410 of filter (e.g., zero) data.

Although certain example methods and apparatus have been described herein, the scope of coverage of this patent is not limited thereto. On the contrary, this patent covers all methods, apparatus, and articles of manufacture fairly falling within the scope of the appended claims either literally or under the doctrine of equivalents.

We claim:

1. A spectrometer comprising:
a laser source configurable to produce a lased light of a single wavelength directable towards a target substance, the laser source having sufficient power to selectively cause a portion of the target to emit Raman scattering and ablate a portion of the target substance to produce a plasma plume by illumination of said target substance with lased light of the same single wavelength;
a separate remote light collector optically configurable to collect light emitted from the portion of the target emitting Raman scattering and from the portion of the target producing the plasma plume;
a filter optically coupled to the remote light collector to remove reflected light and Rayleigh-scattered light;
a spectroscope optically coupled to the filter and configured to separate the collected and filtered light into a frequency spectrum comprising a Raman spectrum and a laser-induced breakdown spectrum;
and an electronic light sensor to record the frequency spectrum.

2. A spectrometer as defined in claim 1, wherein the laser source is a pulsed laser source.

3. A spectrometer as defined in claim 1, wherein the filter is a notch filter.

4. A spectrometer as defined in claim 1, wherein the remote light collector is a telescope or a suitable lens.

5. A spectrometer as defined in claim 1, wherein the single wavelength of the lased light is selected from the group consisting of 248 nm, 266 nm, 532 nm, 785 nm, 830 nm, and 1064 nm.

6. A method of spectroscopy comprising:
using a laser source to produce lased light of a single wavelength;
focusing the lased light;
directing the lased light towards a target;
causing a portion of the target to emit Raman scattering by excitation with said lased light of a single wavelength;
causing a portion of the target to produce a plasma plume by excitation with said lased light of a single wavelength;
remotely detecting the emitted Raman scattering and plasma plume in a single remote collector;
filtering the detected Raman scattering and plasma plume to remove reflected light and Rayleigh-scattered light;
separating the collected and filtered light into a frequency spectrum comprising a Raman spectrum and a laser-induced breakdown spectrum; and
recording the frequency spectrum
wherein said Ramen scattering and said plasma plume are generated by excitation with lased light of the same single wavelength.

7. A method as defined in claim 6, wherein said lased light has a single wavelength selected from the group consisting of 248 nm, 266 nm, 532 nm, 785 nm, 830 nm, and 1064 nm.

8. A method as defined in claim 6, wherein the emitted Raman scattering and plasma plume is detected via at least one of a telescope or a suitable lens.

9. A method as defined in claim 6, wherein said laser source comprises a pulsed laser source.

10. The method of claim 1, wherein said lased light has a single wavelength of 532 nm.

11. The method of claim 6, wherein said lased light has a single wavelength of 532 nm.

12. The method of claim 6, wherein said emitted Raman scattering and plasma plume are detected simultaneously.

* * * * *